United States Patent
Colditz

[11] 3,995,163
[45] Nov. 30, 1976

[54] NEUTRON THERAPY APPARATUS

[75] Inventor: Johannes Karl Ewald Colditz, Eindhoven, Netherlands

[73] Assignee: U.S. Philips Corporation, New York, N.Y.

[22] Filed: Feb. 13, 1975

[21] Appl. No.: 549,523

[30] Foreign Application Priority Data
Feb. 25, 1974 Netherlands ....................... 7402505

[52] U.S. Cl................................. 250/506; 250/515; 250/518
[51] Int. Cl.² ...................... G21F 5/00; G21C 11/00
[58] Field of Search ........... 250/501, 502, 499, 518, 250/496, 503, 506, 515

[56] References Cited
UNITED STATES PATENTS

| | | | |
|---|---|---|---|
| 2,287,620 | 6/1942 | Kallmann et al.................. | 250/501 |
| 3,778,627 | 12/1973 | Carpenter........................... | 250/502 |
| 3,781,564 | 12/1973 | Lundberg............................ | 250/518 |

FOREIGN PATENTS OR APPLICATIONS

| 1,125,111 | 3/1971 | United Kingdom................. 250/518 |
|---|---|---|

*Primary Examiner*—Harold A. Dixon
*Attorney, Agent, or Firm*—Frank R. Trifari; Ronald L. Drumheller

[57] ABSTRACT

The portion of the shield of a neutron radiation apparatus which is situated nearest to the neutron source is made of tungsten. As a result, a commonly used outer shielding layer consisting of a heavy metal can be dispensed with, so that improved shielding and a substantial saving as regards weight are combined.

7 Claims, 1 Drawing Figure

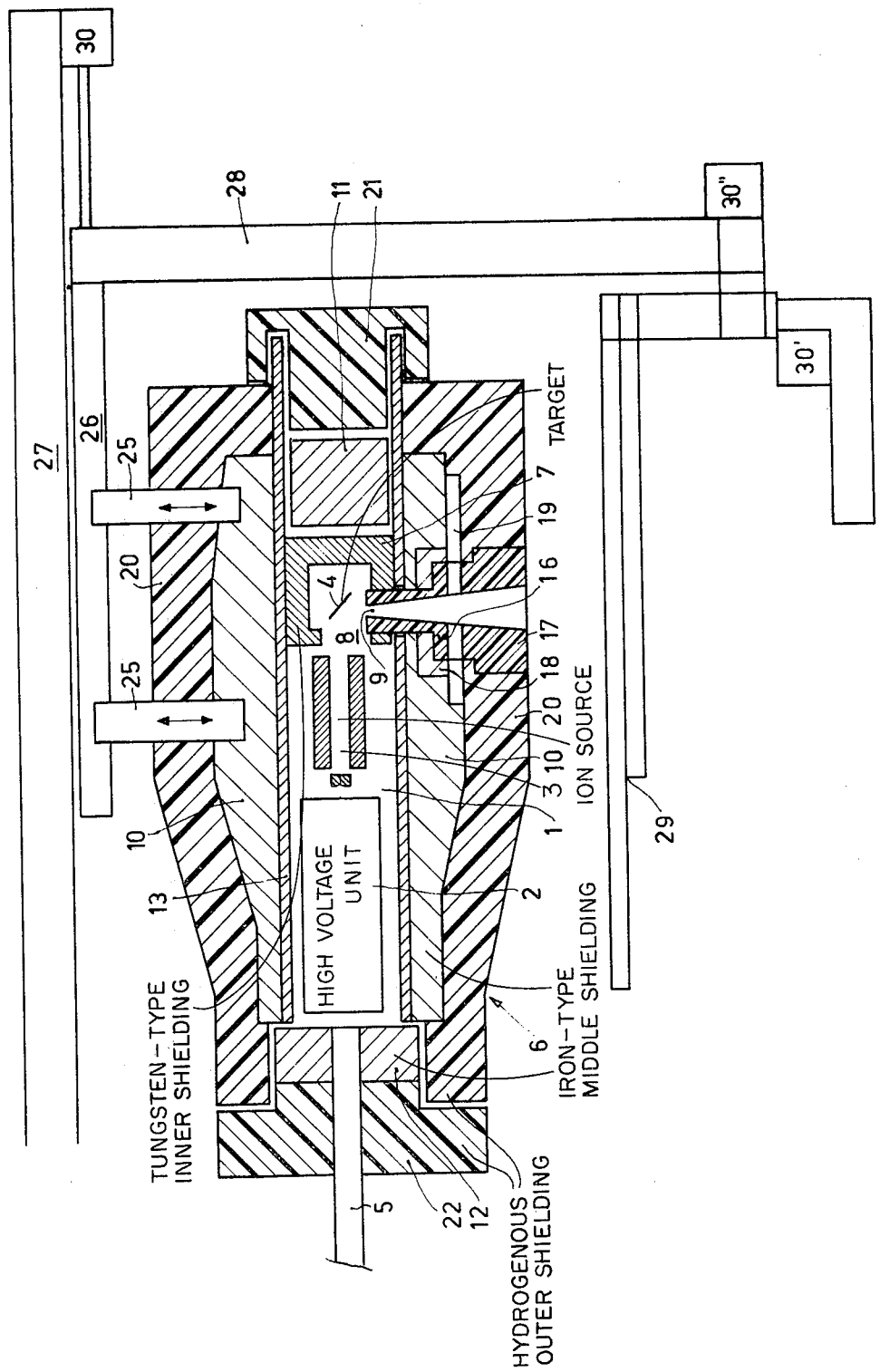

NEUTRON THERAPY APPARATUS

The invention relates to a neutron therapy apparatus provided with a multiple shield which is arranged about a space for a neutron source.

A neutron therapy apparatus of this kind is known, for example, from Netherlands patent application No. 7014076. The shield of the apparatus described therein consists of successively an inner layer which decelerates high-energetic neutrons, an intermediate layer which further decelerates the decelerated neutrons and which intercepts these neutrons, and an outer layer which absorbs the gamma radiation generated during the interception and deceleration of the neutrons. It was found that the intermediate layer, often containing borium, lithium or another suitable element in order to enhance the interception of neutrons, provides better neutron interception, but the overall radiation transmission of neutrons and gamma radiation is not reduced thereby. Because the intermediate layer is comparatively thick, the outer layer makes a comparatively large contribution to the overall weight of the shield.

The invention has for its object to eliminate these drawbacks and to provide a neutron therapy apparatus in which improved shielding against all kinds of radiation is realized without the overall weight of the shield being increased. To this end, a neutron therapy apparatus of the kind set forth according to the invention is characterized in that the shield successively comprises, starting from the neutron source, a layer containing a heavy metal having a highly active work function for high-energetic neutrons, a layer containing a material having a highly active work function for elementary radiation generated in the first layer, and a layer containing an hydrogenous material.

Even though the inner layer of the shield according to the invention contains an additional element, the overall weight of the shield is certainly not increased, because the comparatively heavy outer layer of known shields can now be dispensed with.

In a preferred embodiment, the inner layer is made of tungsten, the subsequent layer of iron and the hydrogenous layer which is now situated on the outer side is made of polythene. When use is made of a shield according to the invention, the neutron transmission as well as the gamma transmission, and hence the overall radiation transmission, is lower than in the case of known shields. An additional important advantage is that the inner layer now has substantial gamma absorption. Consequently, the source is better shielded for this radiation and the radiation level outside the shield is much lower also after the apparatus has been switched off. In addition, the inner layer shields the radiation aperture against radiation from the shield itself, particularly against gamma radiation generated in the iron layer.

A preferred embodiment of a neutron therapy apparatus according to the invention will be described in detail hereinafter with reference to the drawing.

FIG. 1 is a diagrammatic sectional view of a neutron therapy apparatus according to the invention.

A neutron therapy apparatus as shown in FIG. 1 comprises a neutron source 1, having a high voltage unit 2, an ion source 3 and a target 4. Ions generated in the ion source are accelerated in the direction of the target by an electrical potential difference of, for example, 250 kV. The ions release neutrons in the target. In commonly used medical therapy apparatus $T(d, n)^4$ He neutrons having an energy of approximately 14 MeV are thus generated in a tritium target using the known nuclear reaction. The neutron source comprises a supply cable 5 and is accommodated in an envelope 6. The envelope 6 comprises a first shield 7, which is in this case made of tungsten. The shield 7 can also be made of an element of the group having the atomic number 73 – 79, i.e. the elements Ta, W, Re, Os, Ir, Pt, Au or of a combination or an alloy of these elements. In comparison with Fe, having the atomic number 26 and commonly used as a shielding material for the inner layer, all these elements have a comparatively high atomic number. The material for the inner shield according to the invention has, besides a highly active work function for inelastic collision with the high-energetic neutrons, a highly active work function for the absorption of gamma radiation. The inner shield is arranged about the target 4 as closely as possible and encloses the target as completely as possible but for an aperture 8 for the admission of the ion beam and one or more apertures 9 for the passage of a neutron beam to be used. Provided about the inner shielding layer 7 is a subsequent shielding layer 10, in this case made of iron but which may also consist of other materials such as nickel, copper, alloys or combinations of these metals. This layer completely conforms to the inner layer of known shields and serves to decelerate the high-energetic neutrons by inelastic dispersion. As far as the deceleration of the neutrons is concerned, this layer is, therefore, a continuation of the tungsten layer in the preferred embodiment according to the invention. As is diagrammatically shown, this shielding layer also comprises plugs 11 and 12 which cover apertures required for exchanging and operating the neutron source. On the inner side the shield 10 adjoins a sleeve 13 which suitably defines a space 14 for mounting a neutron tube. In order to prevent the exposure of the operating staff and patients to undesired radiation escaping via the opening 9, this opening is provided with additional shields. To this end, in the embodiment shown a diaphragm 16 of tungsten and adjacently a diaphragm 17 of polyethylene is provided. Arranged about the diaphragm 16 is an iron ring 18, and a space 19 accommodates a slide (not shown) which is preferably made of tungsten or lead. The slide can also be constructed as a double layer of lead and tungsten, the tungsten then preferably facing the source. By means of this slide, the aperture 9 can be fully closed when the apparatus is in the switched off condition. In this case the use of tungsten for the shielding material for the diaphragm 16 offers the additional advantage that the gamma radiation is substantially reduced also during the exposure of the patient. The diaphragms 16 and 17 are constructed to be exchangeable as usual, so that the radiation aperture 9 can be adapted to the object to be exposed. A series diaphragm which is known per se can alternatively be incorporated, the various apertures thereof being usable as radiation apertures as desired, and being incorporated in a rotatable, cylindrical portion of the shield for this purpose. It is then advantageous to make the shield 7 used in this case also rotatable, so that a single radiation aperture therein suffices. Provided about the shield 10 is a shielding layer 20 containing an hydrogenous material in which the neutrons are thermalized and intercepted. This shield is preferably made of polythene, and comprises plugs 21 and 22 like the shield 10. In a shield according to the invention, the polythene need not contain a material intercepting neutrons such as borium, lithium or similar. However, for certain geometries of the shield, it may be advantageous according to the invention to provide such a material in the polythene layer, but preferably only in an inner layer thereof.

The envelope 6 is connected to a beam or rail 26 by way of fasteners 25, the height of which can be adjusted. The rail 26 is connected again to a suspension device 27 comprising a column 28. Connected to the column 28 is a patient table 29. Using electric motors 30 or one central drive motor, the neutron source, i.e. the envelope 6, can perform all movements with respect to the patient table which are necessary for the neutron therapy. This suspension and adjusting mechanism can, of course, aso be constructed completely in accordance with known apparatus, so it need not be further elaborated herein.

Because the entire envelope 6 is also shifted and rotated during the adjustments before the radiation, it is of major importance that it is not heavier than absolutely necessary for optimum shielding. A comparatively large saving in weight is achieved according to the invention in that the outer layer, consisting of iron or lead, of the known shield is dispensed with. A second saving can be achieved in this respect by shaping the shield according to the invention on the basis of homogeneous shielding, viewed from the radiation occurring outside the shield. To this end, the local thickness for the other shielding layers can be determined by calculations based on a given neutron source shielded by the tungsten. The tapered exterior shape of the shield as well as the shape of the iron layer result therefrom. Similarly, the optimum thickness of the plugs, disphragms and the tungsten shield used can be calculated. Alternatively, given preferential directions with respect to other directions can be given priority, for example, for the benefit of the operating personnel or the patient. The importance of the material having can perhaps best be illustrated on the basis of a few dimensions of the shield. For example, in a preferred embodiment the diameter of the space for the neutron source is approximately 300 mm, the thickness of the tungsten shield is approximately 75 mm, the thickness of the iron layer is approximately 200 mm, and the thickness of the polythene layer is also approximately 200 mm. The maximum cross-section of the envelope is, therefore, slightly more than 1 meter at a length of slightly more than 1.5 meters.

What is claimed is:

1. A shield for a neutron radiation source for reducing neutron and gamma radiation to harmless levels without a heavy outer shield of lead or iron, comprising:
    a first inner shielding layer consisting essentially of a heavy metal selected from the group consisting of tantalum, tungsten, rhenium, osmium, iridium, platinum and gold, or an alloy thereof;
    a second shielding layer outside of said first layer consisting essentially of a metal selected from the group consisting of iron, nickel and copper, or an alloy thereof; and
    a third outer shielding layer outside of said second layer comprising a hydrogenous material.

2. A shield as defined in claim 1 wherein said first shielding layer consists essentially of tungsten.

3. A shield as defined in claim 1 wherein said second shielding layer consists essentially of iron.

4. A shield as defined in claim 3 wherein said first shielding layer consists essentially of tungsten.

5. A shield as defined in claim 4 wherein said third shielding layer comprises polythene.

6. A shield as defined in claim 1 wherein said third shielding layer comprises polythene.

7. A shield as defined in claim 1 wherein said third shielding layer contains a material having a high work function for thermal neutrons.

* * * * *